United States Patent [19]

Goldring

[11] Patent Number: 4,684,245
[45] Date of Patent: Aug. 4, 1987

[54] ELECTRO-OPTICAL COUPLER FOR CATHETER OXIMETER

[75] Inventor: Stanley D. Goldring, Cupertino, Calif.

[73] Assignee: Oximetrix, Inc., Mountain View, Calif.

[21] Appl. No.: 791,705

[22] Filed: Oct. 28, 1985

[51] Int. Cl.⁴ .............................................. G01N 33/48
[52] U.S. Cl. .................................. 356/41; 350/96.20; 364/416
[58] Field of Search ............... 250/226, 227; 350/96.1, 350/96.15, 96.20, 96.24; 356/41; 364/416; 604/53; 128/653, 656, 665

[56] References Cited

U.S. PATENT DOCUMENTS 4,322,164  3/1982  Shaw .................................. 356/41 X
4,453,218  6/1984  Sperinde et al. ..................... 364/416

*Primary Examiner*—Eugene R. Laroche
*Assistant Examiner*—Steven J. Mottola
*Attorney, Agent, or Firm*—Martin L. Katz; Allan J. Sternstein; Robert W. Stevenson

[57] ABSTRACT

An optical module couples a fiberoptic catheter to a catheter oximeter processing apparatus. The module includes a plurality of LED's for coupling the electrical control signals from the processor and converting them to light signals to transmit to the catheter. The module also includes the means to convert the received reflected light signals from the catheter to electrical signals to be transmitted to the processor. The module further includes a memory to store calibration signals and other data so that the module and catheter can be disconnected from the processor and used with a different processor without necessitating a recalibration.

10 Claims, 3 Drawing Figures

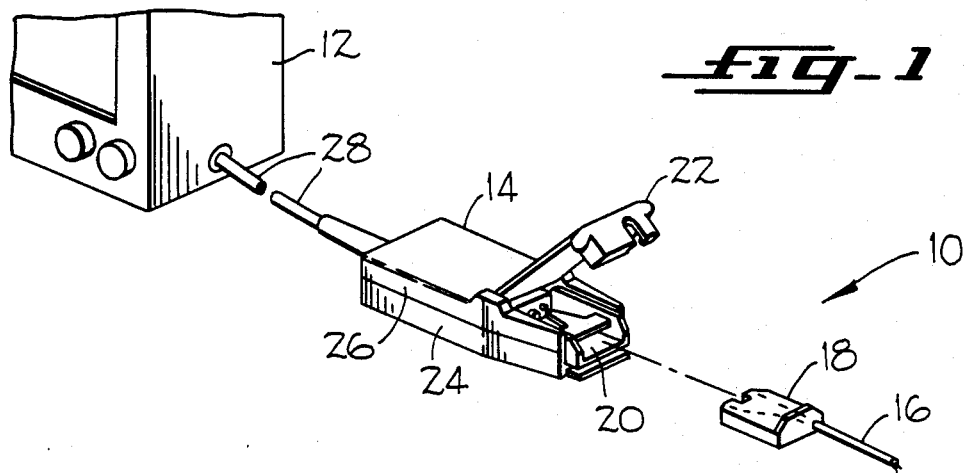
fig_1
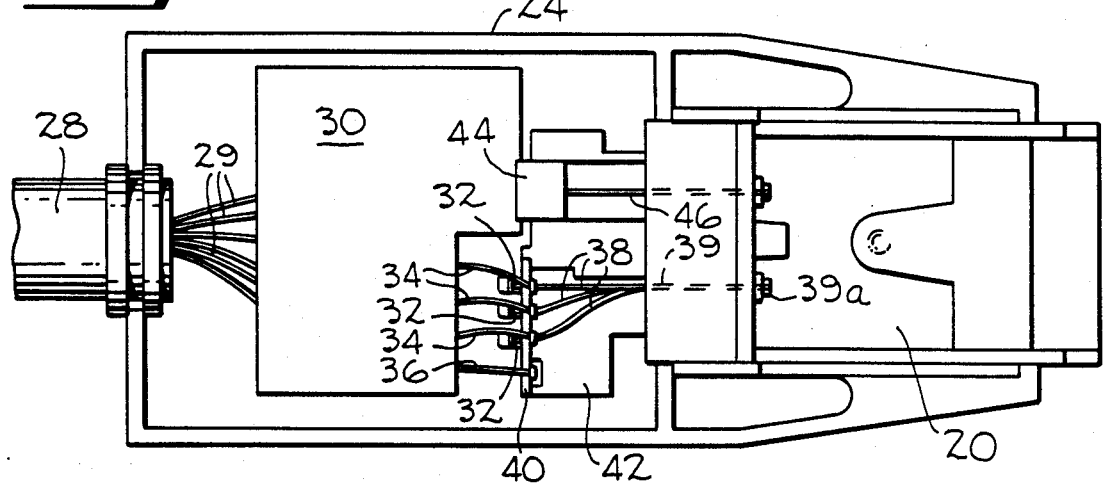
fig_2
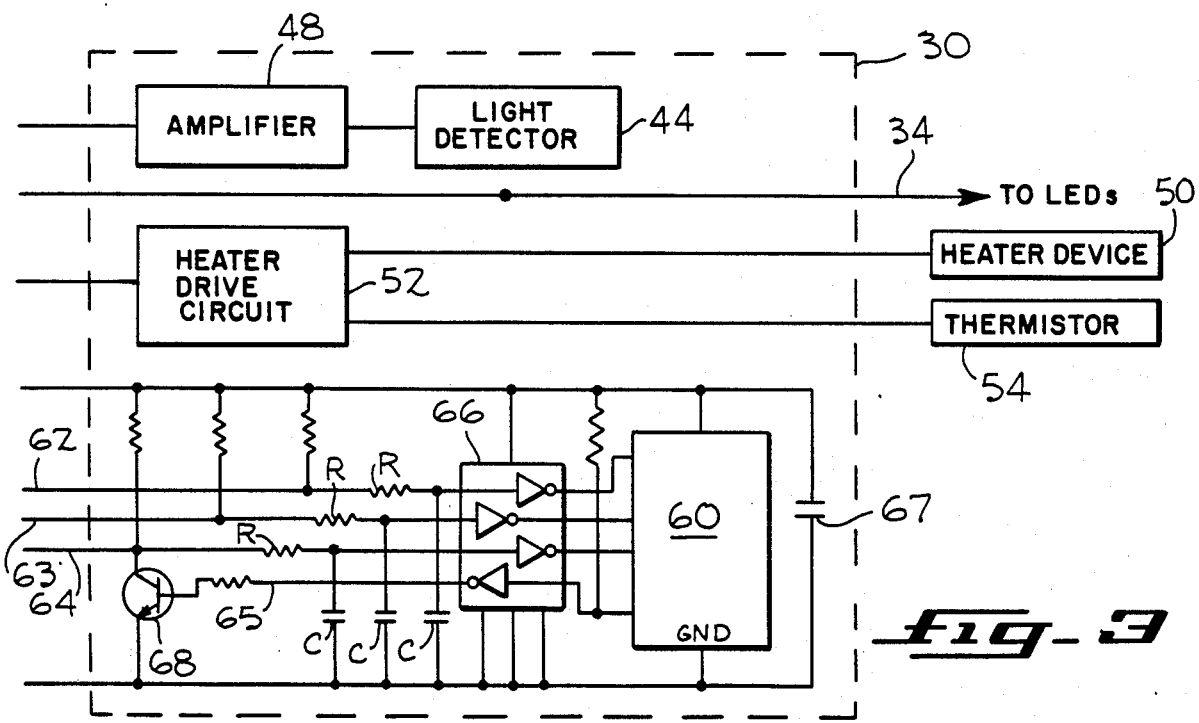
fig_3

ELECTRO-OPTICAL COUPLER FOR CATHETER OXIMETER

BACKGROUND OF THE INVENTION

1. Field of the Invention

This invention relates to an optical module that connects a catheter to a processor in a catheter oximetry system, and more particularly, it relates to optical modules of the readily portable type that can remain with the inserted catheter and the patient as the patient is transferred from one location to another.

2. Description of the Prior Art

A catheter oximetry system provides accurate, continuous, real-time measurement of mixed venous oxygen saturation using multiple wavelength reflection spectrophotometry. The color of red blood cells progressively changes from scarlet to purple as the amount of oxygen that the red blood cells are carrying decreases. When light of different selected wavelengths illuminates the blood, the amount of light backscattered, or reflected, at each wavelength depends upon the color, and therefore, oxygen level of the blood. Careful choice of wavelengths in the transmittal light allows accurate measurement of oxygenated hemoglobin with minimal interference by other blood characteristics such as temperature, pH, and hematocrit.

Approximately 98% of the oxygen in the blood is chemically combined with hemoglobin in red blood cells. The absorption of red and infrared light is substantially different for oxygenated and deoxygenated hemoglobin, and it varies for different wavelengths of light within this red/infrared spectrum. Therefore, the relative amounts of oxygenated hemoglobin and deoxygenated hemoglobin in the blood can be determined by measuring the relative absorption of light at different selected wavelengths. The percentage of hemoglobin which is in the oxygenated form is defined as the oxygen saturation of the blood in the equation:

$$\text{Oxygen Saturation} = \frac{HbO_2}{Hb \times HbO_2} \times 100$$

where $HbO_2$ is the oxygenated hemoglobin concentration and $Hb$ is the deoxygenated hemoglobin concentration.

A widely used catheter oximetry system consists of three basic components: (1) a disposable fiberoptic pulmonary artery catheter that has a distal end adapted to be inserted into a vein or artery of a patient and that interfaces at its other end with (2) an optical module containing light-emitting diodes, a photodetector and associated electronics which, in turn, interfaces with the electrical leads of (3) a computer-based instrument that performs all of the data processing and control functions with displays, alarms and associated read-out devices.

The optical module in the aforedescribed system thus plays the important part of providing the electro-optical connection between the processor, where all of the electronic processing and computations are carried out, and the catheter, which serves as a transmitting guide for the individual light pulses and a receiving guide for the light backscattered (reflected) from the patient's blood. The optical module is comprised of an enclosure or housing having therewithin a plurality of (e.g., three) light-emitting diodes to provide discrete light sources at the selected wavelengths available for performing the oxygen saturation measurements. Light from each of the LED sources is sequentially transmitted in short pulses under the control of electrical signals from the processing apparatus through a transmitting light guide at the connector end of the catheter to illuminate the blood flowing past the catheter tip at the other end. This illuminating light is absorbed, refracted and reflected by the blood, and a portion of the reflected light is collected by the aperture of a second receiving light guide at the catheter tip. This collected light is returned through the catheter to a photodetector in the optical module. The photodetector converts these received light signals to electrical signals which are amplified and transmitted to the processing apparatus over the electrical connections to the module. Using the relative intensities of the signals representing the light levels at the various different wavelengths, the processor calculates oxygen saturation and outputs this information to the user.

Because the actual light levels which can be collected from the backscattered light in the blood are very low, and because the differences in the relative intensities at the different wavelengths are small, variables in the optical system are extremely critical, and the optical module/catheter combination must be carefully calibrated each time it is used so that it can be normalized to some standard in order to provide usable output readings. For example, differences in the transmitting properties of each of the light guides and differences in signal output of the LED's can significantly affect the relative signal levels and hence the end calculations.

In order to accommodate the foregoing problem, it is conventional to first make a calibration reading of the catheter by attaching it to a processor/optical module combination and generating light signals into and receiving reflected light signals back from some known standard reference material as, for example, a reference block which might be packaged with the catheter. This information then remains with the processor and is used to adjust the output readings it receives from the optical module in order to provide accurate and usable data for the doctor or nurse monitoring the patient's blood condition. However, it frequently is the case that a patient may be moved from one area of the hospital to another, e.g., from the operating room to a recovery room or from a recovery room to a hospital room, with the catheter/optical module combination remaining with the patient but with different processors being utilized with such combination at each of the different locations. When this occurs, a totally new calibration must be obtained since the new processor will not have the relevant calibration information, thus hindering the flexibility of use of the oximetry system and adding to the total time and cost of hospital care.

SUMMARY OF THE INVENTION

With the present invention, an optical module is provided for serving as the electro-optical coupling between the fiberoptic catheter and the catheter oximeter processing apparatus in a catheter oximetry system. The module includes an enclosed housing for receiving in light-tight engagement one end of the catheter having the exposed transmitting and receiving light guides. The module is also adapted to receive and provide suitable connections for a plurality of electrical leads from the processing apparatus. Means are provided in the housing for receiving the appropriate control signals from the electrical leads and for creating light signals at a plurality of different wavelengths for direction into the transmitting light guide of the catheter. Means are also provided for receiving the reflected light signals from the receiving light guide and for converting these to electrical signals for connection to the electrical leads and further processing by the processing apparatus.

An important feature of the optical module of the present invention is a memory located in the housing and connected to the electrical leads so that it can receive and store the calibration signals from the processing apparatus after this apparatus has calibrated the module/catheter combination during the initial set-up of the system. With this arrangement, the catheter and optical module may remain with a patient as he is transferred from location to location within the hospital with the calibration for this particular combination of elements remaining with the module so that when the module is reconnected to a different processing apparatus no further calibration is necessary. Thus, the present invention will result in a more efficient use of hospital time and personnel than similar modules and oximetry systems of the prior art.

BRIEF DESCRIPTION OF THE DRAWING

FIG. 1 is a broken perspective view of a catheter oximetry system that includes an optical module embodying the present invention.

FIG. 2 is a plan view of the optical module with the upper housing half removed so as to expose the components within the housing enclosure.

FIG. 3 is a schematic view of the circuitry and component connections located within the body of the optical module.

DESCRIPTION OF THE PREFERRED EMBODIMENT

With reference to FIG. 1, a catheter oximetry system, indicated generally by reference numeral 10, is shown to include a processor 12, an optical module 14, and a fiberoptic catheter 16. The catheter has at one end thereof an optical connector plug 18 that is adapted to slide into a mating receptacle 20 in the optical module. A hinged, spring-loaded cover 22 holds the catheter's optical connector plug in a fixed, generally light-tight position within the receptacle. The optical module itself has a housing formed by a lower half 24 and an upper half 26 which together form an enclosure within which the optical-to-electrical connections for transmission and receiving are made. These halves are tightly clamped together during assembly of the module so that the space provided therewithin is adequate for mounting and maintaining the various electro-optical components of the module. The optical module is electrically connected to the processor by a cable 28 which, as will be seen, includes a plurality of electrical leads.

Looking now at FIG. 2, which shows the optical module 14 with the upper half 26 thereof removed, it will be seen that the electrical leads 29 from cable 28 are connected to a printed circuit board 30 (this being indicated only diagrammatically in FIG. 2).

Three LED light sources 32 provide the light signal pulses at the different wavelengths which pulses are serialized and arranged to be transmitted to the catheter. The control of these pulsed light sources is through the processor 12 by means of the electrical leads 29 which are connected through the printed circuit board 30 to leads 34 (shown in FIG. 2) and a ground return 36.

Each of the LED's transmits its light into an individual light conduit 38, and the individual light conduits 38 are uniformly joined together into a single fiberoptic light guide 39 which extends to an exposed end face 39a at the inner wall of the enclosed receptacle 20 where it is adapted to be optically connected with the exposed end of the transmitting fiber in the plug 18 of the catheter. The LED's and the connecting contacts therefor are mounted upon a board 40 which is secured to a heat sink block 42 within the optical module. For a further and more complete description of the LED light sources 32 and their method of operation, reference is made to the pending United States patent application of Beard, Ser. No. 646,794.

Also mounted to the circuit board 30 is a photodetector 44 which receives an input optical light pipe 46 which, similarly to the light guide 39, is arranged to extend from an exposed position within the receptacle 20 where it can interface with the single receiving fiber in the plug 18 when the plug is inserted in the optical module.

The circuitry found on the printed circuit board 30 is diagrammatically shown in FIG. 3. Thus, it will be seen that the electrical signal from the light detector 44 is amplified in an amplifier 48 for transmission to the processor 12. The processor also provides the timed signal pulses to the LED's 32 which are output from the board on the lines 34 (FIG. 2). A heater device 50 is provided to heat the mounting block 42 so as to maintain the LED's 32 at a generally uniform temperature. This is necessary since the output signals from the LED's must be as uniform as possible and not allowed to drift because the relative percentage of light recovered therefrom is very small and the differences in reflectivity at the different wavelengths (upon which the measurements are based) is relatively small. As seen in FIG. 3, a heater drive circuit 52 is provided to drive the heater device, and a thermistor 54 is mounted adjacent to the LED's so that their temperature can be monitored.

It is an important feature of the present invention that the optical module 14 have the capability of storing and maintaining information in a memory, particularly so that the calibration constants for the optical module and catheter combination can be stored directly in the module. With such capability a new processor can be hooked to the module without requiring a recalibration of the system. Thus, an EE-prom integrated circuit chip 60 is provided as shown in FIG. 3. This memory chip 60 will typically comprise a relatively low cost item which will have a storage capacity for up to a dozen or more numbers, provide for read/write/erase operations, be compatible with conventional logic circuitry and power levels, and have non-volatile erase and write capability so that a separate power supply for the memory will not be required. A chip that satisifes this criteria is an NMC9345/COP495 manufactured by National Semiconductor Corporation, Santa Clara, Calif.

The memory chip 60 is arranged to be programmed from the processor 12 after the initial calculations are made to calibrate the optical module/catheter combination. Once the appropriate calculations have been performed, a chip select line 62 is raised to condition the chip 60 to accept the incoming data. Then, the clockline 63 and the data-line 64 are utilized to load the information into the chip. It will be noted that data line 64 is tied to a transistor 68 so that it can be used to both load and unload information from the memory 60 depending on the signal level on line 65 to the transistor base.

Conventional RC circuits are provided to smooth the inputs on each of the lines 62, 63 and 64 and a Hex Schmidt trigger buffering device 66 is provided to insulate the chip from the processor circuitry. A capacitor 67 is provided across the memory chip to provide the appropriate transient current to the memory when needed.

The algorithms which the processor 12 utilizes in determining the oxygen saturation values based on the reflected light intensities from the LED's 32 are set forth in the pending United States patent application Ser. No. 467,087 of John M. Sperinde, filed Feb. 16, 1983, now U.S. Pat. No. 4,623,248 which is incorporated herein by reference for a further and more complete description of the processing and computations performed by the processor. Thus, three LED's 32 are utilized with light being provided at wavelengths of 670 nanometers ($I_1$), 700 nanometers ($I_2$) and 800 nanometers ($I_3$). The LED's are programmed to serially transmit light sequentially in short pulses to the single transmitting fiber of the catheter, and the circuitry which processes the received signal from the catheter is timed correspondingly to distinguish between the different reflected light beams ($I_1$, $I_2$ or $I_3$). In order to eliminate the effects of differing received light intensities as measurements are made, ratios of the received light beams are provided for making all computations with $R_1$ representing the ratio of reflected or back-scattered intensities at $I_1$ and $I_2$ and $R_3$ representing the ratio of reflected intensities at $I_3$ and $I_2$. The oxygen saturation value ($SO_2$) is then calculated (depending on where taken and what the level is) either as $$SO_2 = A_0 + A_1 R_3,$$

or as $$SO_2 = \frac{B_0 + B_1 R_1 + B_2 R_1^2 + B_3 R_3}{C_0 + C_1 R_1 + C_2 R_1 + C_3 R_3}$$

with the constants $A_0$, $A_1$, $B_0$, $B_1$, $B_2$, $B_3$, $C_0$, $C_1$, $C_2$ and $C_3$ being emperically derived and set in the processor circuitry.

As explained previously, due to the extreme sensitivity of the received light levels in providing useful outlet information, each set-up (including catheter and optical module) must be calibrated so that the output information, i.e., oxygen saturation in the blood, computed by the processor 12, will provide accurate and useful information for the user of the system. Thus, when a catheter 16 is plugged into the optical module 14, it is conventional to use a calibration device having known reflectivity characteristics, such as a reference block, to test the relative reflectivity of the particular set-up. Thus, when the processor module and catheter are linked and the reference block is attached to the lead end of the catheter, the reflected light intensities and ratios $R_1$ and $R_3$ computed therefrom are read by the processor. The processor will be set so that the expected readings for $R_1$ and $R_3$ for the reflectivity of the reference block will be unity. The inverse of the actual readings for $R_1$ and $R_3$ thereby become the calibration factors (to be multiplied with the actual readings obtained later), and it is these factors which may be loaded into the memory chip 60 and stored therein for later use should the optical module and catheter combination be disconnected from the processor and used with a different processor.

The memory chip 60 also is arranged to store a number of other useful items. For example, it is conventional to obtain a number of calibration readings if the catheter is used over an extended time period since deposits may form on the calibrator tip, for example, which will change the received light levels in unpredictable ways. Thus, a separate calibration can be stored in the memory chip and compared with the present calibration readings to determine significant changes or the generation of errors in the new readings. In addition, when a calibration reading is taken, the calibrated ratios and the computed oxygen saturation level at calibration are stored in the memory chip while the processor is computing the calibration factors. In addition, the average intensity signal from each of the received beams ($I_1$, $I_2$ and $I_3$) are saved and stored in the memory chip and the difference between the high and low signal in any received beam is also stored. These last bits of information are useful in determining when an error might be occurring when such differences or average signal values change significantly. Finally, a conventional check sum figure is stored to serve as a check on the integrity of the data in the memory chip.

Although the best mode contemplated for carrying out the present invention has been herein shown and described, it will be apparent that modification and variation can be made without departing from what is regarded to be the subject matter of the invention.

What is claimed is:

1. An optical module for coupling a fiberoptic catheter to a catheter oximeter processing apparatus, said module comprising an enclosed housing for receiving in light-tight engagement therewithin the end of the fiberoptic catheter including a transmitting light guide and a receiving light guide, means within said housing for receiving a plurality of electrical leads from said catheter oximeter processing apparatus, means in said housing for receiving control signals from said electrical leads and for transmitting light signals at a plurality of different wavelengths into said transmitting light guide, means in said housing for receiving blood reflected light signals from said receiving light guide and for providing electrical signals representative thereof to said electrical leads, and a memory storage device located in said housing and connected to said electrical leads to receive calibration signals from said processing apparatus upon initial use of said module and catheter combination which calibration signals are indicative of the electro-optical properties of the module and catheter whereby said module and catheter may be disconnected from said processing apparatus by removing said electrical leads from said housing and used with a different processing apparatus without requiring a recalibration.

2. An optical module as set forth in claim 1 wherein said memory storage device comprises an electronically erasable PROM.

3. An optical module as set forth in claim 2 wherein said memory storage device is connected to said electrical leads by a single data line and an electronic switch connected to said data line for switching said data line between an input line and an output line on said PROM.

4. An optical module as set forth in claim 2 including means for insulating said PROM from noise and other signal level fluctuations in said electrical leads.

5. An optical module as set forth in claim 1 wherein said means for transmitting light signals comprises a plurality of LED light sources connected to transmit light along a single module transmitting light guide and wherein said means for receiving blood reflected light signals and providing electrical signals comprises a single module receiving light guide and a photodetector.

6. An optical module as set forth in claim 5 wherein said module transmitting light guide and said module receiving light guide are directed in spaced positions to one end of an enclosed receptacle within the housing, said receptacle being adapted to receive a plug containing the ends of the catheter light guides.

7. In an optical module for coupling a fiberoptic catheter to a catheter oximeter processing apparatus, said module comprising
   an enclosed housing for receiving in light-tight engagement therewithin the end of the fiberoptic catheter including a transmitting light guide and a receiving light guide,
   means within said housing for receiving a plurality of electrical leads from said catheter oximeter processing apparatus,
   means in said housing for receiving control signals from said electrical leads and for transmitting light signals at a plurality of different wavelengths into said transmitting light guide, and
   means in said housing for receiving blood reflected light signals from said receiving light guide and for providing electrical signals representative thereof to said electrical leads,
   the improvement comprising a memory storage device located in said housing and connected to said electrical leads to receive calibration signals from said processing apparatus upon initial use of said module and catheter combination which calibration signals are indicative of the electro-optical properties of the module and catheter whereby said module and catheter may be disconnected from said processing apparatus by removing said electrical leads from said housing and used with a different processing apparatus without requiring a recalibration.

8. In an optical module as set forth in claim 7 wherein said memory storage device comprises an electronically erasable PROM.

9. In an optical module as set forth in claim 8 wherein said memory storage device is connected to said electrical leads by a single data line and an electronic switch connected to said data line for switching said data line between an input line and an output line on said PROM.

10. An optical module as set forth in claim 8 including means for insulating said PROM from noise and other signal level fluctuations in said electrical leads.

* * * * *